United States Patent [19]

Kowalewski

[11] Patent Number: 4,649,914

[45] Date of Patent: Mar. 17, 1987

[54] RAPID SELF-INFLATING TRACHEAL TUBE WITH CONSTANT PRESSURE CONTROL FEATURE

[76] Inventor: Ryszard J. Kowalewski, 109-311 Tait Cres., Saskatoon, Saskatchewan, Canada, S7H 5L6

[21] Appl. No.: 796,692

[22] Filed: Nov. 12, 1985

[51] Int. Cl.⁴ ............................................. A61M 16/04
[52] U.S. Cl. .......................... 128/207.15; 128/207.16; 417/540; 138/90
[58] Field of Search ...................... 128/207.15, 207.16; 604/97, 100; 417/472, 540; 92/91, 92; 138/90, 93

[56] References Cited

U.S. PATENT DOCUMENTS

| | | | |
|---|---|---|---|
| 2,970,749 | 10/1958 | Montague | 417/540 |
| 3,731,692 | 5/1973 | Goodyear | 128/207.15 |

*Primary Examiner*—Howell Kyle L.
*Assistant Examiner*—Randy Citrin

*Attorney, Agent, or Firm*—Stanley G. Ade; Adrian D. Battison

[57] ABSTRACT

A tracheal tube assembly includes a dual balloon system upstream from the tracheal cuff and located externally to the patient. A pre-determined amount of air may be injected through a one-way valve into the innermost balloon which is of relatively low compliance. Expansion of the inner balloon passively expands the high compliance outer balloon. When the inner balloon is preloaded the system is ready for use. Opening of a control valve selectively interconnects the inner balloon with the surrounding relatively high compliance outer balloon via a high resistance inlet and with the tracheal cuff via a low resistance inlet so that the tracheal cuff is preferentially inflated. Equalization of pressure in the system rapidly occurs and this pressure is determined and maintained at a constant level by the characteristics of the high compliance outer balloon. The control switch can be positioned to allow the tube to function in a non-pressure regulated mode as in the conventional tube.

21 Claims, 5 Drawing Figures

RAPID SELF-INFLATING TRACHEAL TUBE WITH CONSTANT PRESSURE CONTROL FEATURE

BACKGROUND OF THE INVENTION

This invention relates to new and useful improvements in tracheal tube assemblies, and particular the inflation assembly thereof.

A tracheal tube is a medical device commonly used in intensive care and during operations under general anaesthesia. It consists of a flexible tube with the distal end surrounded by a cuff. When inserted into the trachea inflation of this cuff seals the tube to the tracheal wall, facilitates ventilation and also secures the patient's airway from aspiration of gastric contents and any other foreign material.

Conventionally, air or other fluid is injected into the tracheal cuff by means of an inflation syringe attached to the pilot balloon. This system has many inherent disadvantages. Manual inflation by syringe is inconvenient, might require the assistance of a second party and delays the inflation of the cuff. It is especially important to protect the patient's airway when the risk of aspiration of gastric contents is high as in anaethesia for Caesarean section, the traumatized patient and operations for acute abdominal conditions. It is in these situations a system is especially indicated which provides rapid and non-manual inflation of the tracheal cuff, eliminating time delay and need for assistance during intubation of the trachea. Over-compression of the tracheal mucosa by the inflated cuff is another problem with the conventional tracheal tube inflation assembly. The pressure is the tracheal cuff can only be estimated crudely by palpation of the pilot balloon. With manual inflation, the tracheal cuff pressure may frequently exceed the desired pressure (approx. 20 mmHg.). Also during general anaesthesia with nitrous oxide, diffusion of nitrous oxide into the tracheal cuff will increase the pressure exerted on the tracheal wall. This results in a high incidence of complications (sore throat, hoarseness and tracheal damage) after removal of the tube. To prevent the foregoing the cuff pressure should be checked and adjusted frequently. This is inconvenient and time consuming and seldom done in practice.

Many attempts have been made in order to endeavour to correct these problems and prior art known to applicants includes the following:

Canadian Pat. No. 1,052,215 (Bazzell et al). This shows a catheter with an inflation indicator for the cuff or cuff balloon. The inflation measuring device includes a collar substantially encompassing the signal member or balloon.

U.S. Pat. No. 4,020,849 (Jackson) discloses a cuff inflation arrangement for tracheal tubes including a connector member incorporating an auxiliary passage having an entrance device for inflating the cuff with breathing air. The cuff is automatically inflated and the filling process terminated at a desire level for retaining sealing pressure in the cuff.

U.S. Pat. No. 4,116,201 (Shah) discloses a catheter with an inflation control valve for controlling the filling of an inflatable balloon through an inflation lumen.

U.S. Pat. No. 4,134,407 (Elan) shows an external pressure-volume monitor for an endotracheal cuff which provides automatic indication of the pressure in the cuff.

U.S. Pat. No. 3,848,605 (Harautuneia et al) discloses an endotracheal tube including a pilo balloon which serves as a low pressure reservoir.

U.S. Pat. No. 3,794,043 (McGinnis) features an endotracheal tube with an inflatable cuff and an associated check valve for controlling the admitting and release of air to an inflatable balloon.

U.S. Pat. No. 3,642,005 (McGinnis) discloses an endotracheal tube including an inflatable cuff which provides for automatic regulation of the air pressure.

U.S. Pat. No. 4,248,222 (Jaeger et al) discloses an endotracheal tube including a relief valve.

Journal of Thoracic and Cardiovascular Surgery 1972, pages 747–756 Magovern et all shows an occluding cuff system with a high-residual volume cuff inflated by a pressure regulating mechanism which utilizes a specially designed external balloon and a pressure regulating valve.

None of the known prior art cited above teaches a completely satisfactory solution and does not address the principal problems involved, namely, rapid self-inflation and constant pressure control.

SUMMARY OF THE INVENTION

The present invention overcomes difficulties inherent with known practice by allowing rapid self inflation of the tracheal cuff with air from a pre-loaded inflation balloon by means of a simple switch. The invention also allows maintenance, in all circumstances, of the pressure in the tracheal cuff at a pre-determined level.

One aspect of the invention is to provide, in a tracheal tube assembly which includes a flexible conduit, an inflation conduit associated therewith, a tracheal cuff surrounding said flexible conduit in sealing relationship therewith, said inflation conduit operatively connecting to said cuff; the improvement comprising in combination an inflation assembly operatively connected to said inflation conduit, said inflation assembly including an inner flexible balloon and an outer flexible balloon surrounding said inner balloon, said outer balloon having a higher compliance then said inner balloon, a one-way inflation and deflation valve in one end of said inner balloon, a selectively operable control valve component movable from an open position to a closed position and vice versa, connected on one side thereof to said inner and outer balloons and on the other side of said inflation conduit, said control valve, when in the closed position, isolating said inner balloon from said outer balloon and said tracheal balloon and when in the open position, connecting said inner balloon with said outer balloon and said tracheal balloon.

Another aspect of the invention is to provide an inflation assembly for tracheal tube assemblies and the like which include a tracheal cuff, comprising in combination an inner flexible balloon of relatively low compliance and an outer flexible balloon of relatively high compliance concentrically surrounding said inner balloon, one end of said outer balloon being sealed to one end of said inner balloon, a one-way inflation and deflation valve operatively connected to said one end of said inner balloon, a selectively operable control valve component movable from a closed position to an open position and vice versa, operatively connected by one end thereof to the other ends of said inner and outer balloons and to said tracheal cuff, said control valve component when in the closed position, isolating said inner and outer balloons and said tracheal cuff from one another, and when in the open position, connecting together said inner and outer balloons and said associated tracheal cuff.

A further advantage of the invention is to provide a device of the character herewithin described which is simple in construction, economical in manufacture and otherwise well suited to the purpose for which it is designed.

With the foregoing in view, and other advantages as will become apparent to those skilled in the art to which this invention relates as this specification proceeds, the invention is herein described by reference to the accompanying drawings forming a part hereof, which includes a description of the best mode known to the applicant and of the preferred typical embodiment of the principles of the present invention, in which:

DESCRIPTION OF THE DRAWINGS

In the drawings like characters of reference indicated corresponding parts in the different figures.

DETAILED DESCRIPTION

Figure 1:
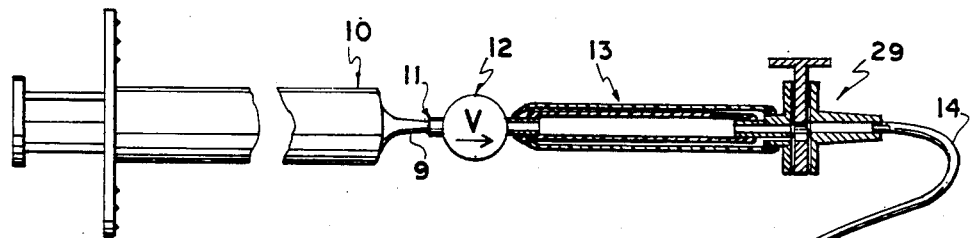
FIG. 1 is a partially schematic view of a tracheal tube assembly with the invention incorporated therein.
Figure 1:
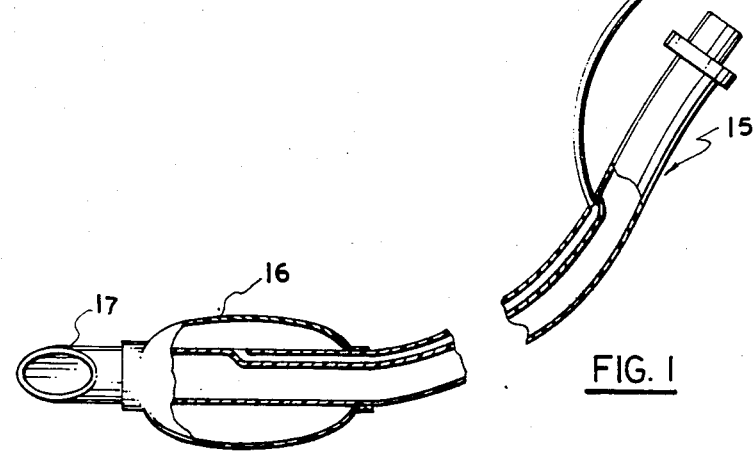

Proceeding therefore to describe the invention in detail, reference should first be made to FIG. 1 in which 10 illustrates a conventional inflating syringe having nozzle 9, selectively engagable with an inlet nozzle 11 of a one-way valve 12 forming part of the invention collectively designated 13 which takes the form of an inflation assembly. This in turn is connected to the flexible inflation conduit 14 associated with the flexible tracheal tube assembly collectively designated 15 terminating with an inflatable cuff 16 surrounding and sealed to the flexible tube assembly 15 adjacent the lower end 17.

The one-way valve assembly 12 includes an inlet nozzle portion 18 to which is secured an inner, elongated cylindrical balloon 19 formed from a suitable material. This inner balloon is sealable secured by one end thereof, around the inner end 18 of the inlet nozzle portion and communicates with the valve 12. This inner balloon is formed from a relatively low compliance material and is of an elongated cylindrical configuration.

Surrounding this inner balloon 19 is an outer balloon 20 sealably secured by one end 21 around the nozzle portion 18 and out board of the one end of the inner balloon 19 so that the outer balloon 20 surrounds the inner balloon in a concentric manner. This outer balloon is made from a resilient material which is of a higher compliance than that of the inner balloon 19 and is also at an elongated cylindrical configuration.

A control valve component collectively designated 29 is provided and takes the form of an inlet nozzle portion 23 around which the other end 24 of the inner balloon is sealably connected as clearly shown.

This forms a major inlet to the control valve component 29.

A port or minor inlet 25 is also provided to the control valve component 29 and the other end 26 of the outer balloon is sealably connected around this minor inlet concentrically with and outboard of the end 24 of the inner balloon. The control valve component 29 includes an outlet nozzle 27 operatively connected to the aforementioned inflation conduit 14 in a conventional manner.

Figure 5:
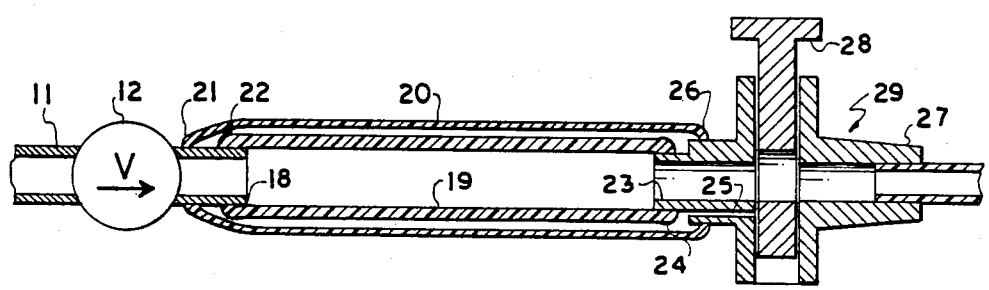
FIG. 5 is a view of the inflation assembly when the control switch is in the intermediate position. The inner "inflation" balloon is in continuity with the tracheal cuff only and there is no pressure regulation. In this mode it functions as a conventional endotracheal tube.
Figure 2:
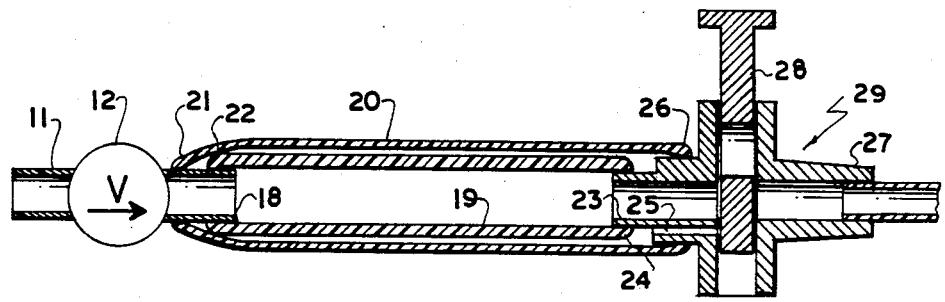
FIG. 2 is a schematic cross-sectional view of the invention shown with the control valve closed and no fluid injected.
Figure 3:
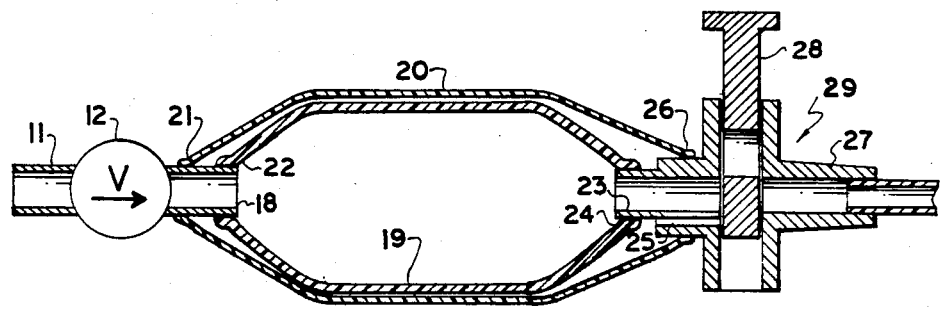
FIG. 3 is a view of the pre-loaded state. The inner "inflation" balloon has been filled with air by attachment of a syringe to the one way valve of the inflation assembly. The control valve is in the closed position. The device is now ready for use.
Figure 4:
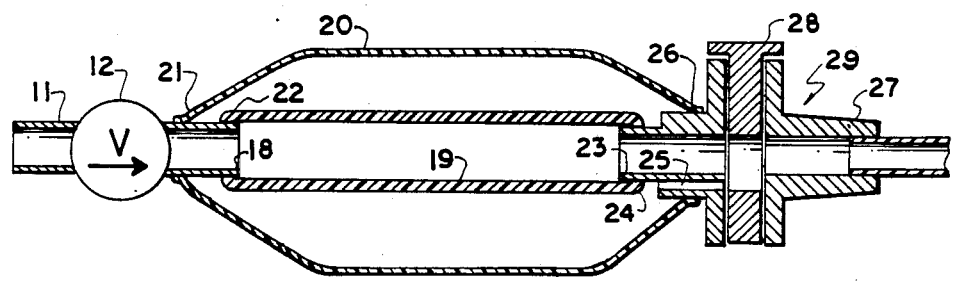
FIG. 4 is a view similar to FIG. 3 but showing the control valve in the open position.

The valve element 28 of the control valve component is shown schematically in FIGS. 2, 3, 4 and 5 and is movable from a closed position shown in FIGS. 2 and 3, and to an open position shown in FIG. 4 and an intermediate position shown in FIG. 5.

When in the closed position, FIGS. 2 and 3, the inner balloon is isolated from the outer balloon with both balloons also being isolated from the tracheal cuff 16.

However, when in the open position shown in FIG. 4, the inner balloon is connected to the interior of the outer balloon via the communication between the major and minor inlets 23 and 25 and is also connected via nozzle 27, to the tracheal cuff 16 so that pressure is equalized between all three chambers.

In operation, the valve 29 is in the closed position as shown in FIG. 2 with the inflation assembly being operatively connected to the cuff as shown in FIG. 1.

The inflating syringe 10 is detachably connected to the inlet of the one-way valve 12 and a sufficient volume of air or other gas is injected into the inner balloon. This expands the inner balloon actively and the outer balloon passively as shown in FIG. 3.

When the endotracheal tube is inserted into the trachea, moving the control valve switch 28 to the open position as shown in FIG. 4 will deflate the inner balloon, transferring air into the tracheal cuff 16 and the outer balloon 20.

Furthermore, the type of control valve 29 is such that the tracheal cuff will inflate preferentially. This will occur because the diameter of the inlet to the outer balloon 25 is smaller than that of the inlet to the tracheal cuff 27.

The outer balloon 20 is of an elongated cylindrical configuration and the entry of additional gas will cause it to elongate rather than increase in diameter. The pressure within the system is determined by the high compliance outer balloon 20.

In circumstances where pressure control is not desired the tracheal cuff can be directly inflated by moving the control valve switch 28 to the middle position. The system then functions as in the conventional manner as shown in FIG. 5.

Deflation of the system is performed in the conventional manner by an insertion of a syringe into the one-way valve 12 and aspiration of the air or fluid.

It will therefore be apparent that there is provided a system with three important new features. First, a rapid inflation of the tracheal cuff, secondly, the self inflation thereof once the control valve is opened and thirdly, the constant maintenance of a predetermined pressure within the tracheal cuff.

Since various modifications can be made in my invention as hereinabove described, and many apparently widely different embodiments of same made within the spirit and scope, it is intended that all matter contained in the accompanying specification shall be interpreted as illustrative only and not in a limiting sense.

I claim:

1. In a tracheal tube assembly which includes a flexible conduit, an inflation conduit associated therewith, a tracheal cuff surrounding said flexible conduit in sealing relationship therewith, said inflation conduit operatively connecting to said cuff; the improvement comprising in combination an inflation assembly operatively connected to said inflation conduit, said inflation assembly including an inner flexible balloon and an outer flexible balloon surrounding said inner balloon, said outer balloon having a higher compliance than said inner balloon, a one-way inflation and deflation valve in one end of said inner balloon, a selectively operable control valve component means movable from an open position to a closed position and vice versa, connected on one side thereof to said inner and outer balloons and on the other said to said inflation conduit, said control valve component means, when in the closed position, isolating said inner balloon from said outer balloon and said tracheal cuff and when in the open position, connecting said inner balloon with said outer balloon and said tracheal cuff.

2. The improvement according to claim 1 in which said inner and outer balloons are concentrically aligned and are sealed by one end thereof around an inner end of the inlet nozzle of said one-way valve, in sealing relationship therewith and with one another.

3. The improvement according to claim 2 in which said inner and outer balloons are secured by the other ends thereof to one side of said control valve component means in sealing relationship therewith.

4. The improvement according to claim 3 in which said one side of said control valve component means includes a major inlet, said inner balloon being connected to said major inlet by the other end thereof, and a minor inlet, said outer balloon being connected to said minor inlet by the other end thereof, said control valve component means, when in the open position, operatively connecting together said major and minor inlets and hence said inner and outer balloons.

5. The improvement according to claim 1 in which said inner and outer balloons are secured by the other ends thereof to one side of said control valve component means in sealing relationship therewith.

6. The improvement according to claim 5 in which said one side of said control valve component means includes a major inlet, said inner balloon being connected to said major inlet by the other end thereof, and a minor inlet, said outer balloon being connected to said mnior inlet by the other end thereof, said control valve component means, when in the open position, operatively connecting together said major and minor inlets and hence said inner and outer balloons.

7. The improvement according to claim 5 in which said inner and outer balloons are of an elongated cylindrical configuration.

8. The improvement according to claim 1 in which said control valve component means includes an intermediate position whereby said inner balloon is operatively connected to said tracheal cuff and is isolated from said outer balloon thereby operating as a conventional endotracheal tube.

9. A tracheal tube assembly comprising in combination a flexible conduit, an inflation conduit associated therewith, a tracheal cuff surrounding said flexible conduit in sealing relationship therewith, said inflation conduit being operatively connected to said cuff, an inflation assembly operatively connected to said inflation conduit, said inflation assembly including an inner flexible balloon and an outer flexible balloon surrounding said inner balloon, said outer balloon having a higher compliance then said inner balloon, a one-way inflation and deflation valve in one end of said inner balloon, a selectively operable control valve component means movable from an open position to a closed position and vice versa, connected on one side of said inner and outer balloons and on the other side to said inflation conduit, said control valve component means, when in the closed position, isolating said inner balloon from said outer balloon and said tracheal cuff and when in the open position, connecting said inner balloon with said outer balloon and said tracheal cuff; whereby self inflation of said cuff when said inner balloon is actively inflated thereby passively inflates said outer balloon.

10. A tracheal tube assembly according to claim 9 in which said inner and outer balloons are concentrically aligned and are sealed by one end thereof around an inner end of the inlet nozzle of said one-way valve, in sealing relationship therewith and with one another.

11. A tracheal tube assembly according to claim 10 in which said inner and outer balloons are secured by the other ends thereof to one side of said control valve component means in sealing relationship therewith.

12. A tracheal tube assembly according to claim 9 in which said inner and outer balloons are secured by the other ends thereof to one side of said control valve component means in sealing relationship therewith.

13. A tracheal tube assembly according to claim 12 in which said one side of said control valve component means includes a major inlet, said inner balloon being connected to said major inlet by the other end thereof, and a minor inlet, said outer balloon being connected to said minor inlet by the other end thereof, said control valve component means, when in the open position, operatively connecting together said major and minor inlets and hence said inner and outer balloons whereby, when said inner balloon is actively inflated, said outer balloon is passively inflated.

14. A tracheal tube assembly according to claim 13 in which said inner and outer balloons are of an elongated cylindrical configuration.

15. The tracheal tube assembly according to claim 9 in which said control valve component means includes an intermediate position whereby said inner balloon is operatively connected to said tracheal cuff and is isolated from said outer balloon thereby operating as a conventional endotracheal tube.

16. An inflation assembly for tracheal tube assemblies and the like which include a tracheal cuff, comprising in combination an inner flexible balloon of relatively low compliance and an outer flexible balloon of relatively high compliance concentrically surrounding said inner balloon, one end of said outer balloon being sealed to one end of said inner balloon, a one-way inflation and deflation valve operatively connected to said one end of said inner balloon, a selectively operable control valve component means movable from a closed position to an open position and vice versa, operatively connected by one end thereof to the other ends of said inner and outer balloons and to said tracheal cuff, said control valve component means when in the closed position, isolating said inner and outer balloons and said tracheal cuff from one another, and when in the open position, connecting together said inner and outer balloons and said associated tracheal cuff; whereby self-inflation of said cuff occurs when said inner balloon is actively inflated thereby passively inflating said outer balloon.

17. An inflation assembly for tracheal tube assemblies including a tracheal cuff according to claim 16 in which said inner and outer balloons are concentrically aligned and are sealed by one end thereof around an inner end of the inlet nozzle of said one-way valve, in sealing relationship therewith and with one another.

18. An inflation assembly for tracheal tube assemblies including a tracheal cuff according to claim 16 in which said inner and outer balloons are secured by the other ends thereof to one side of said control valve component means in sealing relationship therewith.

19. An inflation assembly for tracheal tube assemblies including a tracheal cuff according to claim 17 in which said one side of said control valve component means includes a major inlet, said inner balloon being connected to said major inlet by the other end thereof, and a minor inlet, said outer balloon being connected to said minor inlet by the other end thereof, said control valve component means, when in the open position, operatively connecting together said major and minor inlets and hence said inner and outer balloons.

20. An inflation assembly for tracheal tube assemblies including a tracheal cuff according to claim 19 in which said inner and outer balloons are of an elongated cylindrical configuration.

21. The inflation assembly according to claim 16 in which said control valve component means includes an intermediate position whereby said inner balloon is operatively connected to said tracheal cuff and is isolated from said outer balloon thereby operating as a conventional endotracheal tube.

* * * * *